United States Patent
Mordant

(10) Patent No.: US 11,376,355 B2
(45) Date of Patent: Jul. 5, 2022

(54) CANNULA, ECMO ASSISTANCE SYSTEM

(71) Applicant: ASSISTANCE PUBLIQUE HOPITAUX DE PARIS, Paris (FR)

(72) Inventor: Pierre Mordant, Paris (FR)

(73) Assignee: ASSISTANCE PUBLIQUE HOPITAUX DE PARIS, Paris (FR)

( * ) Notice: Subject to any disclaimer, the term of this patent is extended or adjusted under 35 U.S.C. 154(b) by 521 days.

(21) Appl. No.: 16/349,865

(22) PCT Filed: Nov. 14, 2017

(86) PCT No.: PCT/EP2017/079219
§ 371 (c)(1),
(2) Date: May 14, 2019

(87) PCT Pub. No.: WO2018/091474
PCT Pub. Date: May 24, 2018

(65) Prior Publication Data
US 2020/0054817 A1    Feb. 20, 2020

(30) Foreign Application Priority Data

Nov. 15, 2016  (FR) ......................... 1661037

(51) Int. Cl.
*A61M 1/36*  (2006.01)
*A61M 1/16*  (2006.01)
(Continued)

(52) U.S. Cl.
CPC ......... *A61M 1/3659* (2014.02); *A61L 29/085* (2013.01); *A61M 1/1603* (2014.02);
(Continued)

(58) Field of Classification Search
CPC ............ A61L 29/085; A61L 2300/236; A61L 2300/42; A61M 1/1603; A61M 1/1629;
(Continued)

(56) References Cited

U.S. PATENT DOCUMENTS 4,114,618 A * 9/1978 Vargas ................. A61M 25/02
                                                 604/165.01
5,171,218 A   12/1992 Fonger et al.
(Continued)

FOREIGN PATENT DOCUMENTS

WO   WO 2011/161146 A1   12/2011
WO   WO 2016/137212 A1    9/2016

OTHER PUBLICATIONS

International Search Report as issued International Patent Application No. PCT/EP2017/079219, dated Feb. 14, 2018.

*Primary Examiner* — Benjamin J Klein
(74) *Attorney, Agent, or Firm* — Pillsbury Winthrop Shaw Pittman LLP

(57) ABSTRACT

A cannula for the circulation of a fluid in an artery, includes a main lumen conveying a volume of fluid towards a first distal end; an accessory lumen including at least one inner portion arranged inside the main lumen, including: a proximal end situated downstream from the proximal end of the main lumen so as to capture a fraction of the flow of fluid entering the main lumen; a bent portion modifying the direction of flow of the fluid flow captured by the accessory lumen with respect to the direction of flow of the fluid emerging from the first end; a second distal end situated upstream from the first distal end of the main lumen, emerging on a side opening of the cannula so as to direct the captured fraction of liquid in the modified direction of flow.

12 Claims, 4 Drawing Sheets

(51) Int. Cl.
*A61M 1/26* (2006.01)
*A61L 29/08* (2006.01)
*A61M 39/24* (2006.01)

(52) U.S. Cl.
CPC ........ *A61M 1/1629* (2014.02); *A61M 1/1698* (2013.01); *A61M 1/267* (2014.02); *A61M 39/24* (2013.01); *A61L 2300/236* (2013.01); *A61L 2300/42* (2013.01); *A61M 2039/2406* (2013.01); *A61M 2039/2426* (2013.01); *A61M 2205/0238* (2013.01); *A61M 2205/3334* (2013.01); *A61M 2205/3337* (2013.01); *A61M 2206/11* (2013.01)

(58) Field of Classification Search
CPC .. A61M 1/1698; A61M 1/267; A61M 1/3659; A61M 25/0029; A61M 25/007; A61M 39/24; A61M 2025/0039; A61M 2025/0073; A61M 2039/2406; A61M 2205/0238; A61M 2205/3334; A61M 2205/3337; A61M 2206/11
See application file for complete search history.

(56) References Cited

U.S. PATENT DOCUMENTS

| | | | | |
|---|---|---|---|---|
| 6,099,506 | A * | 8/2000 | Macoviak | A61M 25/06 604/173 |
| 6,110,139 | A * | 8/2000 | Loubser | A61M 1/3613 604/30 |
| 6,953,655 | B1 * | 10/2005 | Hassanein | A01N 1/02 435/1.1 |
| 9,220,872 | B2 * | 12/2015 | Ravikumar | A61M 25/02 |
| 10,449,286 | B2 * | 10/2019 | Cho | A61M 1/3659 |
| 2012/0259273 | A1 * | 10/2012 | Moshinsky | A61M 25/0043 604/28 |
| 2016/0121079 | A1 * | 5/2016 | Walther | A61M 25/0043 604/264 |

* cited by examiner

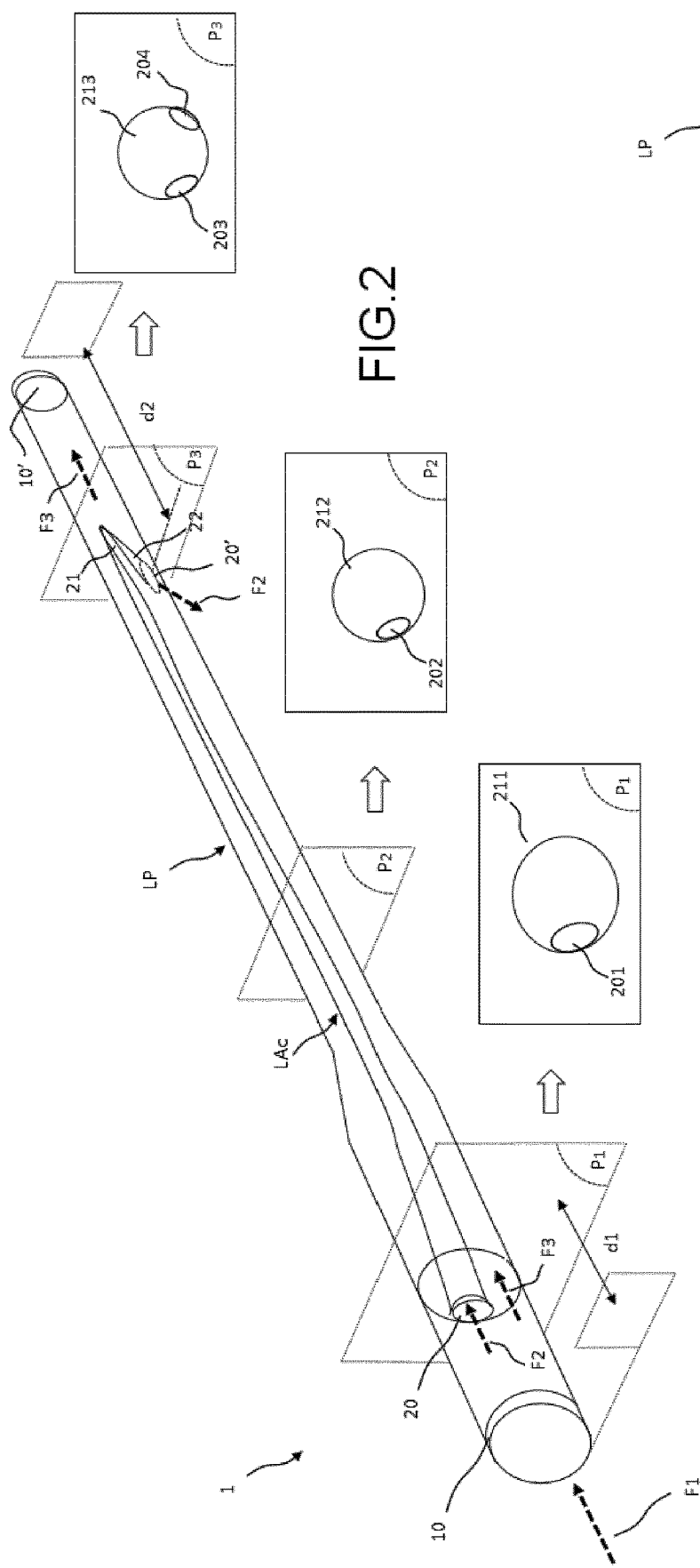
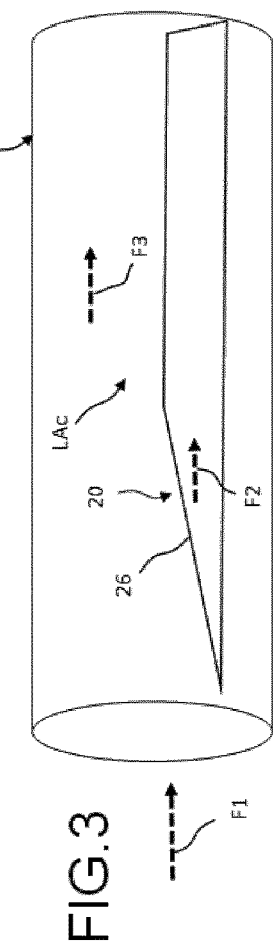
FIG.2
FIG.3

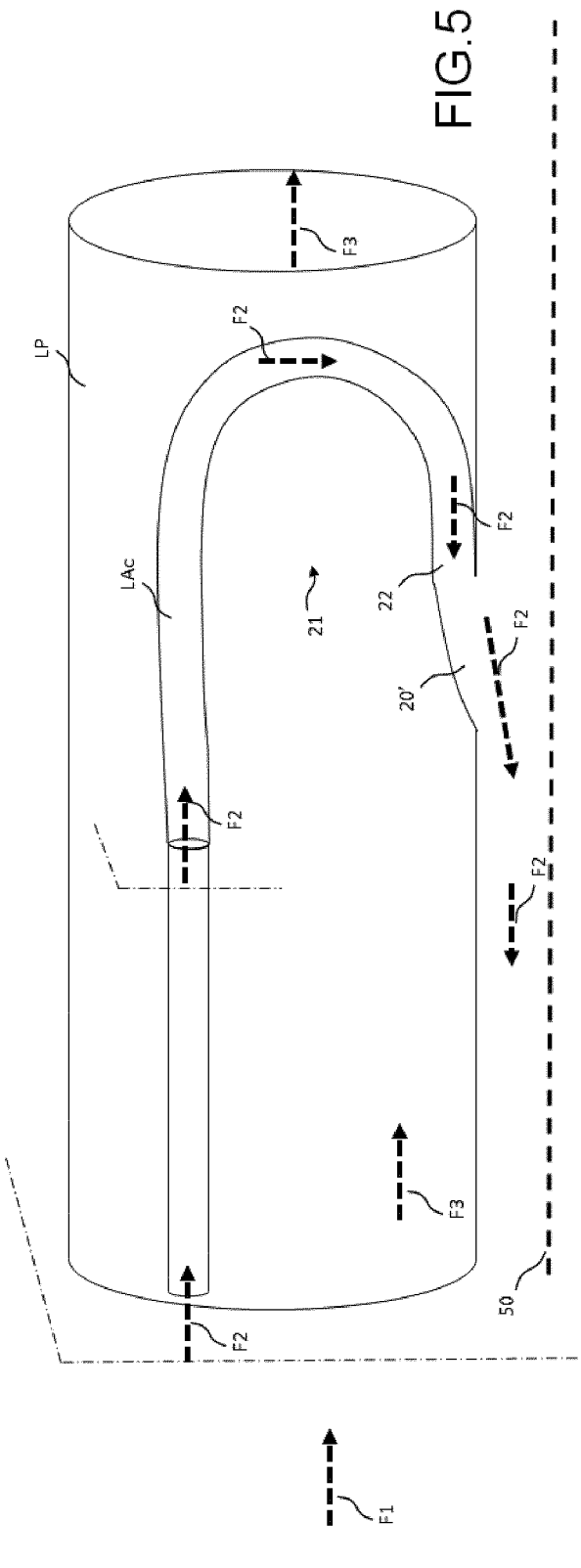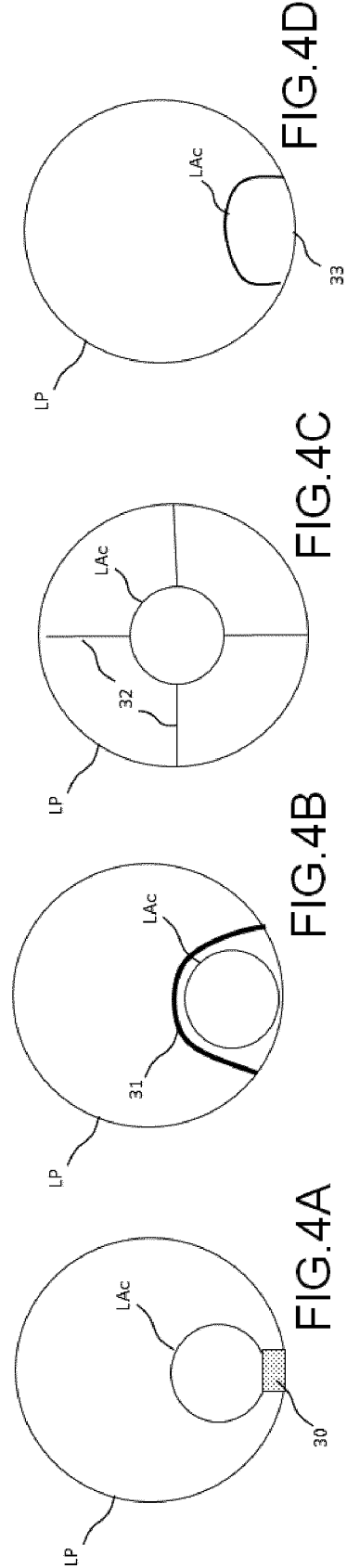

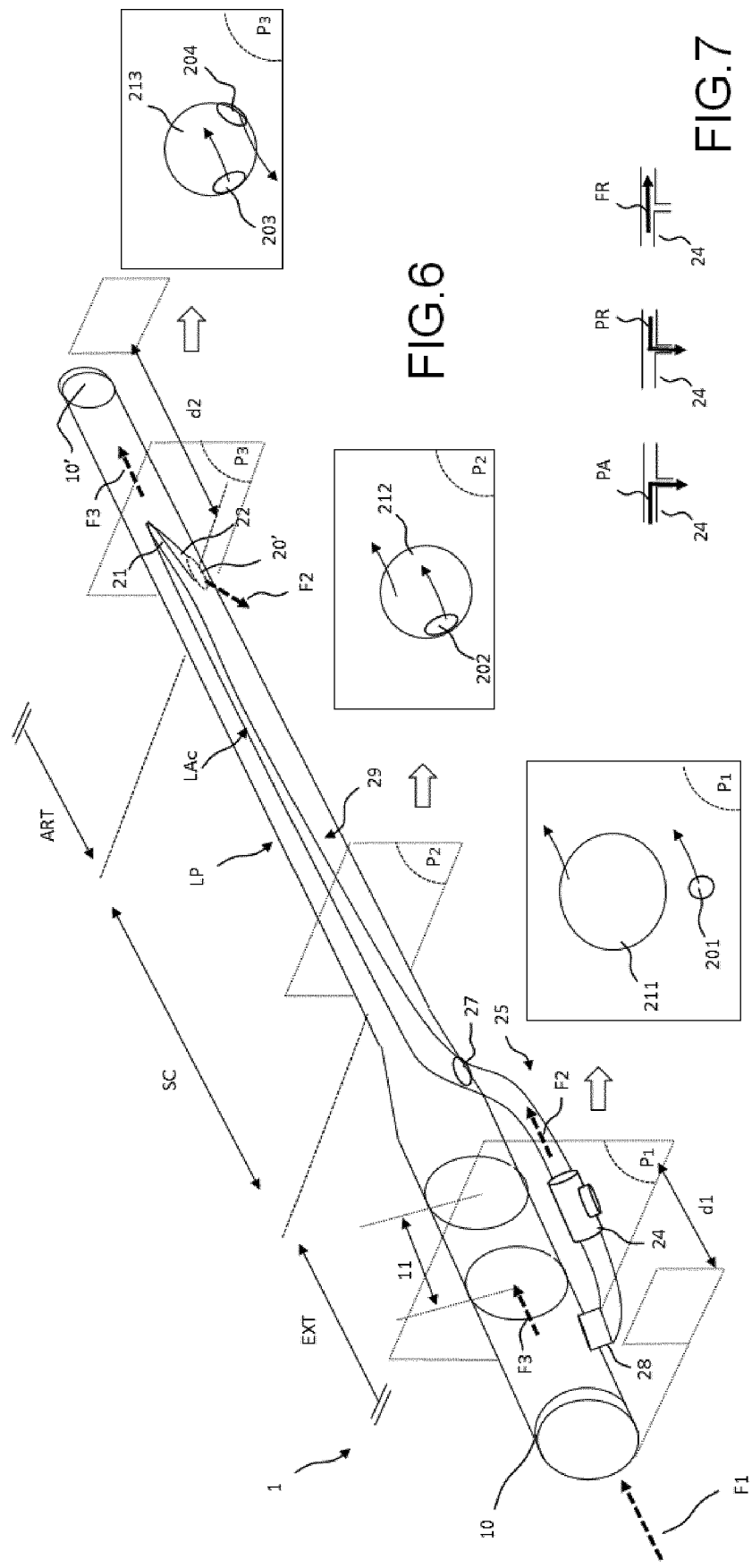

CANNULA, ECMO ASSISTANCE SYSTEM

CROSS REFERENCE TO RELATED APPLICATIONS

This application is the U.S. National Stage of PCT/EP2017/079219, filed Nov. 14, 2017, which in turn claims priority to French Patent Application No. 1661037 filed Nov. 15, 2016, the entire contents of all applications are incorporated herein by reference in their entireties.

TECHNICAL FIELD OF THE INVENTION

The present invention concerns a cannula for injection of a fluid in an organ, an arterial or venous blood vessel, a lymphatic vessel or a bronchial structure. More specifically, the field of the invention relates to cannulas for extracorporeal systems allowing oxygenation of a blood flow which is sampled and reintroduced into an organ or vessel identical to or different from the organ or vessel where the sample was taken. More specifically, the field of the invention relates to cannulas for dECMO (Extra Corporeal Membrane Oxygenation) systems allowing oxygenation of a blood flow which is taken and reintroduced into an organ or vessel. Finally, the invention relates in particular to ECMO-VA (veno-arterial) devices allowing a first volume of oxygenated blood to be conveyed in an artery in the retrograde direction, and a second volume of oxygenated blood to be conveyed in the said artery in the anterograde direction.

TECHNOLOGICAL BACKGROUND OF THE INVENTION

Cannulas exist today which are associated with devices for oxygenation using an extracorporeal membrane, known by the acronym ECMO. These cannulas enable a volume of blood to be extracted using a pump, in order to inject a volume of blood which has been processed extracorporeally in order to oxygenate it. A wide variety of cannulas exist, depending on the desired applications, which can in particular be veno-venous VV or veno-arterial VA, or alternatively veno-arterio-venous VAV. These cannulas enable the blood to flow in a closed circuit due to a technique to oxygenate a volume of blood which has a low level of oxygen, taken from a body.

ECMO-VA, which stands for "Extra Corporeal Membrane Oxygenation—Veno Arterial", is a reference treatment for a refractory cardiogenic shock, for a refractory cardiac arrest, and for decompensation of primitive or secondary arterial hypertension. It is a favoured technique in the case of low haemodynamic or respiratory tolerance of lung transplantation, heart transplantation, and all thoracic, pulmonary or cardiovascular surgery.

An ECMO includes a set of components enabling a volume of blood to be extracted from an organ or vessel, to be oxygenated, decarboxylated, possibly heated, and then to be reinjected when artificially oxygenated into an organ or vessel.

It is referred to as a "peripheral ECMO-VA" when the injection of oxygenated blood is made into a peripheral artery, not into the aortic root or into the pulmonary artery (central ECMO-VA).

The peripheral ECMO-VA circuit generally includes an inflow cannula which is preferentially positioned in a large-diameter vein, first heparin tubing, a centrifugal pump, an oxygenation and decarboxylation membrane, second heparin tubing, and an injection cannula which is also preferentially placed in a large-diameter artery.

A problem which is currently experienced concerns the positioning of the arterial injection cannula in a peripheral artery due to a high risk of arterial occlusion and therefore of ischaemia of a limb, such as an arm or a leg. Typically, when the injection cannula is inserted into the axillary artery or the femoral artery, it can lead to a risk of reduction of the downstream flow rate caused by the presence of the cannula and by the creation of a retrograde arterial flow. The notions of "downstream" and "retrograde" are defined relative to the physiological direction of circulation of the blood.

Reducing the downstream flow rate can then lead to an impairment of the arterial flow of perfusion of the limb and create limb ischaemia. This consequence is particularly pronounced if haemodynamics is impaired and/or if haematosis is impaired and/or if collateral development is limited.

If the iatrogenic limb ischaemia is not treated it can lead to a rhabdomyolysis, renal insufficiency, dialysis and death. If it is treated too late, it can be necessary to perform discharge aponeurotomies, and possibly to amputate the limb.

Currently, to mitigate the consequences of limb ischaemia using peripheral ECMO-VA, a second cannula, called a reperfusion cannula, can be connected in a Y-connection to the arterial line of the ECMO. This second cannula is implanted in the anterograde direction, downstream from the main cannula, which is generally implanted in the retrograde direction.

However, since this technique uses two cannulas of different diameters, which must be implanted in two different locations of the artery, in two different directions, it has disadvantages.

Firstly, it is a long procedure and sometimes requires different medical staff, and additional imaging techniques, arteriography using radioscopy, or vascular Doppler ultrasound examination. It also complicates the installation of the ECMO in a context which is often urgent, since there are two puncture sites in the artery. Indeed, the two cannulas must be implanted in different directions, and must be handled taking precautions. They also have different calibres, of 20 G to 6 F, in the case of the reperfusion cannula, and 15 F to 18 F in the case of the injection cannula. Another disadvantage is that the reperfusion cannula can cause additional complications in the patient, such as distal emboli, dissection of the artery, thrombosis of the artery, or haematoma at the puncture site.

SUMMARY OF THE INVENTION

The invention enables the above-mentioned disadvantages to be resolved.

One object of the invention concerns a cannula for circulation of a fluid in an artery, characterised by the fact that it includes:
- A main lumen, conveying a volume of fluid to a first distal end;
- A secondary lumen, containing at least one inner portion positioned inside the main lumen, and partly extending parallel to the latter over a portion of the length of the main lumen, where the said secondary lumen includes:
  - a proximal end located downstream from the proximal end of the main lumen, so as to divert a fraction of the incoming flow rate of the fluid in the main lumen;

an elbow portion modifying the direction of flow of the flow rate of fluid diverted by the secondary lumen relative to the direction of flow of the fluid emerging from the first end;

a second distal end upstream from the first distal end of the main lumen, flowing out through a lateral aperture of the cannula, so as to direct the said diverted fraction of the liquid in the modified flow direction, where the second distal end of the secondary lumen corresponds to the lateral aperture.

One advantage is that this limits the arterial occlusion effect and therefore the limb ischaemia effect. This solution eliminates the need to install a reperfusion cannula, which is difficult to put in place. In addition, the fact that there is a second distal end, corresponding to a lateral aperture in a wall forming the main lumen of the cannula, enables the substantial risk of arterial occlusion and therefore of ischaemia to be reduced. Indeed, by inserting a secondary lumen into an artery the passing section of the blood is reduced, and this can cause a thrombus or an occlusion. The fact that the portion of the secondary lumen is not outside the cannula prevents the section of the artery from being reduced, and therefore prevents a risk of thrombus or occlusion.

According to one embodiment, the elbow portion is designed so as to guide the flow diverted by the secondary lumen in a direction which is roughly opposite the flow flowing towards the end of the main lumen.

According to one embodiment, the main lumen has a diameter of 15 F to 20 F, i.e. of 5 to 7 mm, and the secondary lumen has a diameter of 20 G to 6 F, i.e. of 0.9 to 2 mm. One advantage of this is that this enables an anterograde flow rate to be generated upstream from the injection in the retrograde direction of the main lumen of the cannula, to limit the risks of ischaemia in the upstream part of the limb.

According to one embodiment, the secondary lumen has a circular or elliptical section.

According to one embodiment, the proximal and/or distal end of the secondary lumen is bevelled, such that the section of the proximal and/or distal aperture of the secondary lumen is contained in a plane which is not orthogonal to the axis of one of the two lumens. One advantage of this is that it "laminarises" the blood flow at the entrance of the secondary lumen, and reduces turbulence.

According to one embodiment, the secondary lumen has a longitudinal portion attached along a portion of the inner surface of the main lumen. One advantage of this is that it enables the secondary lumen to be held in position.

According to one embodiment, the secondary lumen is formed from a single inner portion contained within the volume of the main lumen.

According to one embodiment, the secondary lumen also includes a portion external to the main lumen positioned upstream from the inner portion, where the said outer portion has a drain valve and is intended to be an extracorporeal portion of the cannula.

According to one embodiment, the outer portion of the secondary lumen contains a first junction positioned in contact with the lateral surface of the main lumen, and a second junction positioned in contact with the lateral surface of the main lumen. The outer portion enables a fraction of the liquid to be conveyed towards the first distal end of the main lumen outside the said main lumen between the two junctions. This fraction which is conveyed outside the main lumen can be drained due to the presence of the drain valve.

One invention also concerns a cannula for circulation of a fluid in an artery, where the cannula includes:

a main lumen including a first distal end and a first proximal end, where the main lumen conveys a volume of fluid according to a length between the first proximal end and the first distal end;

a secondary lumen including
at least one inner portion positioned inside the main lumen, extending partly parallel to the latter over a portion of the length of the main lumen,
a proximal end located downstream from the proximal end of the main lumen, so as to divert a fraction of the incoming flow rate of the fluid in the main lumen;
an elbow portion modifying the direction of flow of the flow rate of fluid diverted by the secondary lumen relative to the direction of flow of the fluid emerging from the first end;
a second distal end located upstream from the first distal end of the main lumen, emerging outside the main lumen, characterised by the fact that the secondary lumen also includes a portion external to the main lumen positioned upstream from the inner portion, where the outer portion of the secondary lumen has a portion which allows the light to pass inside the outer portion, and where this outer portion of the secondary lumen is intended to be an extracorporeal portion of the cannula. Thus, when the cannula is put in position the user can see whether the second distal end is in the artery, due to the fact that the blood passes up in this lumen, and therefore is passing in the outer portion allowing the light to pass.

According to one embodiment, the outer portion of the secondary lumen allowing the light to pass extends along the entire length of the outer portion.

According to one embodiment, the outer portion of the secondary lumen is translucent or transparent.

The fact that it is transparent also enables the operator to be helped to estimate the flow rate of the fluid by visual means.

According to one embodiment, the outer portion of the secondary lumen includes a drain valve.

According to one example of this embodiment, the valve has at least one closed state, enabling the fluid to pass from the distal end of the secondary lumen to the proximal end of the secondary lumen (in one direction or in the other), and a drain state preventing the fluid from passing from the distal end of the secondary lumen to the proximal end of the secondary lumen. Thus, the fact that the outer portion is translucent or transparent enables the operator to see the fluid, whether in the closed state or in the open state.

In this example the valve includes a drain outlet. This drain outlet is designed to be connected to a pipe.

According to one characteristic, in the drain state the valve includes an anterograde position enabling the fluid to pass the proximal end towards the drain outlet. The operator can therefore check that the blood is flowing satisfactorily from the entrance of the cannula connected to the ECMO circuit towards the secondary lumen.

According to one characteristic, in the drain state the valve can have a retrograde position enabling the fluid to pass the distal end towards the drain outlet. The operator can therefore check that the blood is flowing satisfactorily from the outlet of the cannula positioned in the artery towards the secondary lumen. By assessing this backflow the operator can check that the distal end of the secondary lumen is in a satisfactory inter-arterial position.

According to one characteristic, in the closed state the valve includes an outlet enabling the fluid to pass from the proximal end towards the distal end of the secondary lumen.

According to one embodiment, the secondary lumen has its proximal end inside the main lumen, and its proximal end downstream from the first proximal end is bevelled, such that the section of the proximal aperture of the secondary lumen is contained in a plane which is not orthogonal to the axis of one of the two lumens. One advantage of this is that it "laminarises" the blood flow at the entrance of the secondary lumen, and reduces turbulence.

According to one embodiment, the second distal end is positioned so as to direct the said diverted fraction of the liquid in the modified flow direction;

According to one example of this embodiment, the second distal end is a lateral aperture in a wall forming the main lumen of the cannula.

According to another example of this embodiment, the second distal end includes a portion located outside the wall forming the main lumen. For example, the second distal end can be retracted inside the main lumen to insert and withdraw the cannula in the artery, and operates outside the main lumen.

The various implementations can be combined.

Other characteristics of the cannula described above can also be present in this cannula.

One invention also concerns a cannula including at least:
- a main lumen including a first distal end and a first proximal end, where the main lumen conveys a volume of fluid according to a length between the first distal proximity and the first distal end;
- a secondary lumen including
    - at least one inner portion positioned inside the main lumen, extending partly parallel to the latter over a portion of the length of the main lumen,
    - a proximal end located downstream from the proximal end of the main lumen, so as to divert a fraction of the incoming flow rate of the fluid in the main lumen;
    - an elbow portion modifying the direction of flow of the flow rate of fluid diverted by the secondary lumen relative to the direction of flow of the fluid emerging from the first end;
    - a second distal end located upstream from the first distal end of the main lumen, emerging outside the main lumen, characterised by the fact that the cannula also includes an anti-backflow valve between the distal end of the main lumen and the proximal end of the secondary lumen.

When installing the cannula, this enables blood exiting the cannula through the proximal end of the main lumen to be reduced, or eliminated.

The anti-backflow valve can have an aperture or a slit enabling an introducer to be inserted into it. The introducer therefore traverses the anti-backflow valve. The anti-backflow valve also includes a membrane with the aperture or the slit positioned such that the walls of the membrane close the aperture or the slit when the fluid pushes the membrane to the proximal end of the main lumen.

The membrane is positioned to allow the fluid to flow in the direction from the proximal end of the main lumen to the distal end of the main lumen.

When withdrawing an introducer from the cannula, this also enables the blood flowing out of the cannula to be reduced.

Indeed, it is known to use an introducer which is more rigid than the cannula, and the distal end of which is sharper, to enable to the artery to be damaged less when inserting the cannula in the artery.

The cannula's secondary lumen can also have the portion external to the main lumen and/or the distal end corresponding to the lateral aperture in a wall of the main lumen.

The cannula can also have the characteristic(s) of one or other of the embodiments described above for the previous cannulas.

Another object of the invention concerns an cannula introducer assembly characterised by the fact that it includes one of the three cannulas described above, and an introducer having a portion traversing the main lumen.

Another object of the invention concerns a system for injection of a fluid into an artery, characterised by the fact that it includes:
- One of the three cannulas described above of the invention,
- a pump positioned to pump a predetermined flow rate of fluid from a sampling cannula, cooperating with an inlet of the pump via an interface tube;
- an oxygenator positioned to introduce a proportion of oxygen in a fluid, where an inlet of the oxygenator co-operates with an outlet of the pump via a second interface tube;
- a heat exchanger positioned to inject a fluid at a fixed temperature in the cannula through a third interface tube, where the said exchanger takes the fluid from the oxygenator through a third tube.

According to one embodiment, at least one tube is covered with a layer of heparin.

According to one embodiment, the pump is positioned and configured to establish a drawn blood flow rate.

BRIEF DESCRIPTION OF THE FIGURES

Other characteristics and advantages of the invention will be seen clearly on reading the detailed description below, with reference to the appended figures, which illustrate:

FIG. 2: a perspective view of an embodiment of a cannula of the invention;

FIG. 3. an embodiment representing a portion of a cannula of the invention containing a main lumen and a secondary lumen;

FIGS. 4A to 4D: various implementation variants for holding the secondary lumen inside the main lumen;

FIG. 5: an example embodiment of a junction of a secondary cannula emerging at the periphery of the main cannula, where the said junction is made as an extension of a cut formed by the secondary lumen;

FIG. 6: an embodiment in which the secondary lumen includes a portion external to the main lumen including a drain valve;

FIG. 7 various modes of drain operation which can be implemented using the valve.

DETAILED DESCRIPTION OF EMBODIMENTS OF THE INVENTION

Figure 1:
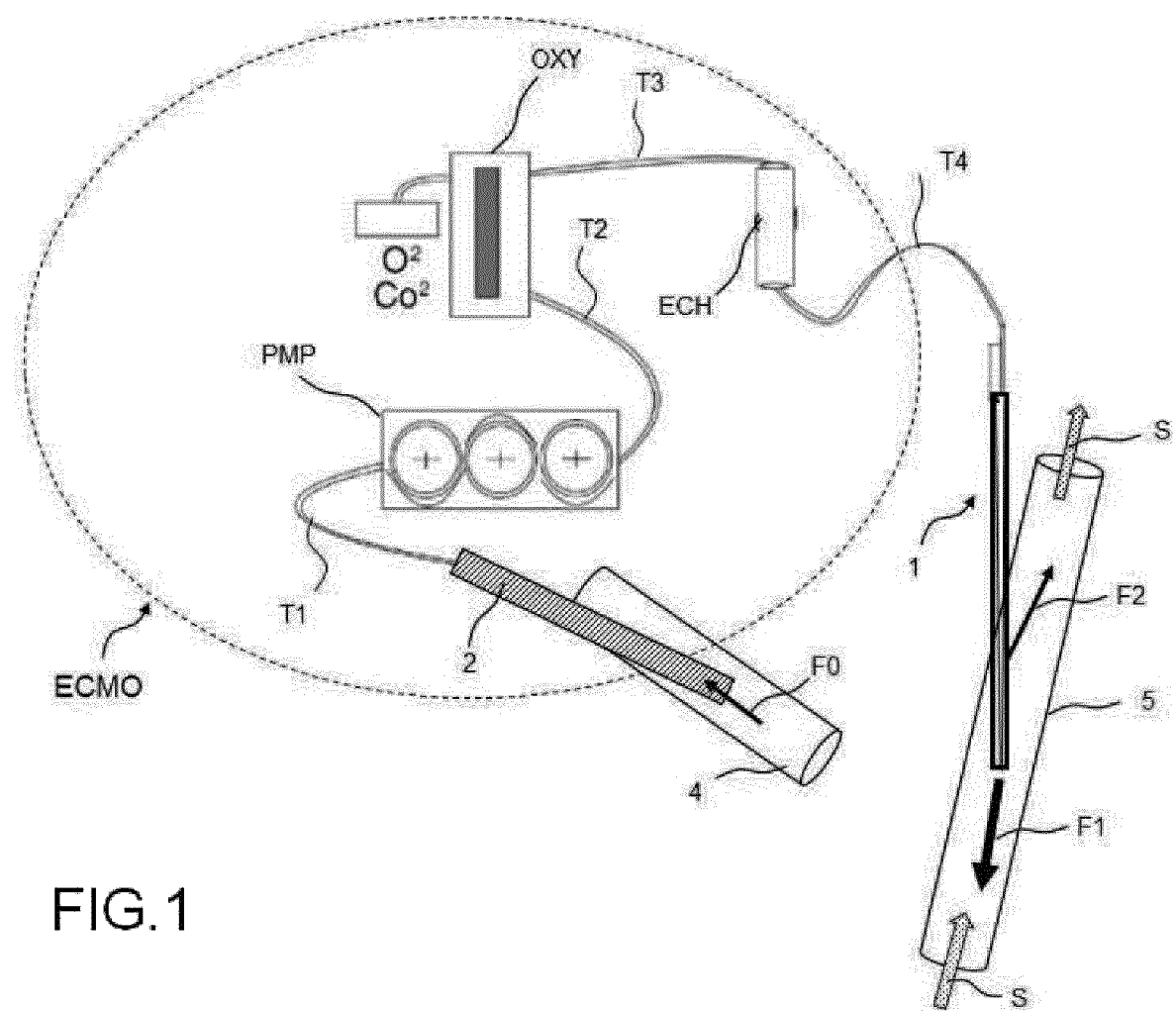
FIG. 1: an ECMO system including an injection cannula of the invention.

In the remainder of the description, an "anterograde flow direction" of a fluid is the name given to: the physiological flow direction of the blood in a vessel or an organ. A "retrograde flow direction" of a fluid is the name given to the reverse flow direction of the blood in a vessel or an organ. The reference system is therefore adopted relative to the physiology of the human or animal body. By extension, and for the sake of clarity of the explanation of the embodiment, we will name the flow direction of main lumen LP: the "retrograde direction" and the flow direction of secondary lumen LAc: the "anterograde direction", where each is considered at its output from cannula 1 when speaking of their direction.

FIG. 1 represents an ECMO system including various components enabling a volume of sampled blood to be oxygenated, and this blood to be re-injected into a vessel of a patient, such as an artery.

A pump PMP has two functions: pumping of the oxygen-depleted and carbon dioxide-rich blood of a vein 4 from inflow cannula 2, together with injection of the oxygenated and decarboxylated blood into an injection cannula 1 to be introduced into an artery 5.

Pump PMP is configured to pump the oxygen-depleted and carbon dioxide-rich blood at a predefined and possibly configurable flow rate. The flow rate must enable effective oxygenation and decarboxylation of the oxygen-depleted and carbon dioxide-rich blood.

Pump PMP is also configured in order that the blood injected in injection cannula 1 arrives roughly at the value of a physiological flow rate according to the patient's condition.

According to one embodiment, the ECMO system includes a tank (not represented). The function of this tank is to regulate the flow rate of treated blood. Inflow cannula 2 takes a volume FO of blood which is conveyed to the tank. According to a second embodiment, this step is accomplished before the pumping step.

According to one example implementation, pump PMP is of the "centrifugal" type. A centrifugal pump PMP uses the rotational motion of a wheel inserted in pump PMP. The movement and the flow rate of the fluid can thus be set and controlled. According to another embodiment the pump PMP has "wheels" and is also called "peristaltic". According to one embodiment, pump PMP generates a drawn flow rate.

Oxygenator OXY includes a membrane which artificially reproduces the function of the alveolar-capillary membrane. This membrane enables gaseous exchanges to be made in order to oxygenate the blood and to eliminate the carbon dioxide contained in the blood by decarboxylation. Oxygenator OXY is connected to pump PMP from which it receives the oxygen-depleted and carbon dioxide-rich blood at a set flow rate.

According to one embodiment, the membrane of oxygenator OXY is flat or tubular. Flat-membrane oxygenators OXY contain silicon membranes or membranes assembled in layers. The tubular membranes consist of composed hollow fibres, for example non-porous polymethylpentenes.

According to one embodiment, the fibres can include a coating which has less resistance to the flow, and facilitates a laminar flow.

Heat exchanger ECH receives the oxygenated and decarboxylated blood from oxygenator OXY in order to heat it. The blood passes through a system enabling the thermal energy of a fluid such as water to the blood, without mixing the two fluids. The heat flux traverses the exchange surface which separates the oxygenated blood and the water. Heat exchanger ECH sets the temperature of the blood in order that it is in the temperature range of the blood flowing in the body of a patient.

Depending on the embodiments, the exchange can be incorporated in the ECMO device or be external to it.

According to one embodiment, heat exchanger ECH is connected to a tank so as to heat the blood after it has been drained; the steps of pumping followed by the steps of oxygenation/decarboxylation are implemented thereafter.

In an alternative manner, according to another embodiment, the heating can come from the oxygenator itself. In this case it advantageously includes resistors included for this purpose.

The aperture of the proximal end of injection cannula 1 is connected to heat exchanger ECH such that it receives the oxygenated, decarboxylated and heated blood. The oxygenated, decarboxylated and heated blood enters into a main lumen LP of injection cannula 1. A fraction of the volume of injected blood is then diverted by a secondary lumen LAc positioned inside main lumen LP in order to be injected into artery 5. The two lumens are positioned such that:
  the flow diverted by secondary lumen LAc is injected in an anterograde direction with a flow F2 into artery 5 and;
  the flow which is not diverted by secondary lumen LAc and continuing in main lumen LP is injected in a retrograde direction with a flow F1 into artery 5.

The blood flow in artery 5 is represented by the "S" arrows in FIG. 1.

Inflow cannula 2, pump PMP, oxygenator OXY, heat exchanger ECH and injection cannula 1 are connected to one another through four interfaces which can take the form of tubes T1, T2, T3 and T4. These tubes T1, T2, T3, T4 are intended to pass the blood, whether or not oxygenated, and whether or not decarboxylated, between the different elements enabling it to be treated.

Tube T1 thus enables the aperture of inflow cannula 2 to be connected to pump PMP. Tube T2 enables pump PMP to be connected to oxygenator OXY. Tube T3 enables oxygenator OXY to be connected to heat exchanger ECH, and tube T4 enables heat exchanger ECH to be connected to the aperture of injection cannula 1. The diameter of each tube T1, T2, T3, T4 is chosen so as to enable the blood to move, while minimising the risk of haemolysis and coagulation. The diameters of tubes T1, T2, T3, T4 are therefore adjusted according to the known flow rates allowing the blood to flow in the body.

According to one embodiment, tubes T1, T2, T3, T4 have a coating of heparin, an anti-coagulant which thus enables the formation of blood clots inside tubes T1, T2, T3, T4 to be prevented.

FIG. 2 represents a perspective view of a cannula of invention 1. According to a preferred usage corresponding to operation with a peripheral ECMO-VA, cannula 1 of the invention is an injection cannula. According to another embodiment, the cannula of the invention could be used as an inflow cannula by using one or two puncture sites to take a volume of blood. In the remainder of the description the embodiment of an inflow cannula is described.

Injection cannula 1 includes a main lumen LP with a proximal end 10 able to cooperate with a connecting aperture from a component of the ECMO, such as for example heat exchanger ECH. A second lumen, called secondary lumen LA, is positioned inside main lumen LP. According to one embodiment, secondary lumen LAc includes a portion which extends in parallel to main lumen LP. In addition, secondary lumen LAc includes an elbow portion 21 emerging in a lateral aperture 20' of main lumen LP.

Positioning of the Two Lumens

According to a first embodiment, secondary lumen LAc is a structural lumen associated from main lumen LP. FIGS. 4A to 4C represent various implementation variants, in each of which a cross-section of each of lumens LAc and LP is represented. In this case, secondary lumen LAc can be attached to main lumen LP by a flexible or rigid attachment 30, 31, 32. According to one embodiment, cannula 1 includes means 30, 31, 32 to hold secondary lumen LAc. For example, the holding means can be attachment rings 31 distributed along a portion of main lumen LP. According to another example implementation, the holding means can be formed from a rail 30 extending along a portion of the two lumens, where secondary lumen LAc and main lumen LP then include, respectively, a longitudinal male connector and respectively a longitudinal female connector or, conversely, cooperating together, so as to connect the two lumens LAc and LP together securely.

According to another implementation variant, secondary lumen LAc is held roughly in the centre of main lumen LP. Holding means 32 form semi-rigid or rigid rods so as to hold secondary lumen LA in position.

According to a second embodiment, secondary lumen LAc is attached to a portion of the inner surface of main lumen LP which extends in the direction of lumen LP. In this embodiment, cannula 1 includes, for example, a double lumen LAc, LP, which can be manufactured by moulding. FIG. 4D represents an example embodiment in which secondary lumen LAc and main lumen LP share a common portion 33 of their surface.

According to another embodiment, secondary lumen LAc can be assembled by bonding within main lumen LP.

According to one embodiment, secondary lumen LAc has a diameter of between 20 G and 6 F. When secondary lumen LAc includes narrowed or widened sections, its greatest diameter or its average diameter is also between 20 G to 6 F. When secondary cannula LAc has a profile other than a circular section profile, such as for example an elliptical profile, a characteristic dimension equivalent to the diameter can characterise the cannula.

This characteristic dimension is then within a dimension equivalent to a diameter of 20 G and 6 F.

Proximal end 20 of secondary lumen LAc is preferentially positioned downstream from proximal end 10 of main lumen LP such that the volume of liquid F2 entering into secondary lumen LAc corresponds to a fraction of a volume F1 flowing upstream from this end. In the present description, notations F1, F2 and F3 represent, interchangeably, a volume of liquid or a flow rate of liquid, depending on the context in which the annotation is used.

According to one embodiment, proximal end 20 of secondary lumen LAc is positioned a few centimetres from proximal end 10 of main lumen LP; for example this distance d1 can be between 5 and 10 cm.

Secondary lumen LAc includes a portion 21 forming an elbow enabling flow F2 of liquid taken from flow F1 to be directed in a direction which is roughly opposite the direction of the flow of liquid F3 which is not taken by secondary lumen LAc, and continuing its course in main lumen LP to distal end 10'. Elbow portion 21 is positioned within main lumen LP and emerges at a lateral aperture 20' of main lumen LP and therefore of cannula 1, which corresponds to distal end 20' of secondary lumen LAc.

This arrangement prevents a protruding portion going beyond main lumen LP. This is particularly desirable when introducing cannula 1 in an artery 5, to prevent any damage to artery 5 with a portion going beyond the wall of cannula 1.

Due to the elbow portion of secondary lumen LAc, the invention therefore has the dual advantage of:
enabling a blood flow F2 to be delivered in the antero-grade direction when introducing cannula 1 into an artery 5 and;
preventing damaging the artery when introducing or removing main lumen LP.

The invention also avoids the need to make a second puncture site of a reperfusion cannula with a Y branch connection to the arterial line. It therefore facilitates the positioning of a peripheral ECMO-VA by having only a single puncture site of cannula 1 to be made.

Elbow portion 21 is represented in FIG. 2. This elbow portion can, depending on the embodiments, be more or less stretched to facilitate the creation of a laminar flow, and to prevent the effects of turbulence caused by elbow 21. According to one embodiment, the curve of elbow 21 is constant over the elbow portion, so as to minimise the effects of variation of curvature on the fluid. In the latter case, elbow portion 21 forms an arc of a circle, or a half-circle, to modify the orientation of fluid F2 in an anterograde direction, i.e. in a direction opposite to the ejection of fluid F3 at output 10' of main lumen LP.

Aperture 20' is appropriate for the diameter or characteristic dimension of secondary lumen LAc. The speed of ejection of fluid F2 can therefore be controlled, depending on the flow rate entering F1 in cannula 1.

FIG. 2 also represents three cross-sections $P_1$, $P_2$ and $P_3$. A first cross-section $P_1$ represents a section 201 of secondary lumen LAc and a section 211 of main lumen LP. The two lumens LAc and LP share a portion of wall, as is represented in FIG. 4D.

A second cross-section $P_2$ represents a section 202 of secondary lumen LAc and a section 212 of main lumen LP. The two lumens LAc and LP share a given portion of wall. It should be noted that in this cross-section the diameters of lumens LAc and LP are made smaller so as to provide a cannula 1 which takes up minimum space when introduced into artery 5. The reduction of the diameters also enables to injected flow rates to be accelerated, as a consequence of reducing the hydrodynamic force which must be supplied by the ECMO.

The narrowing of the two cannulas LAc and LP and the ratio of the sections of the two cannulas LAc and LP enable the speed of ejection of the blood into artery 5 to be controlled, in both directions. Incoming flow rate F1 can therefore be calibrated such that flow rates F3 and F2 correspond to physiological flow rates or compensated physiological flow rates if the fluid enters in an anterograde or retrograde direction.

A third cross-section $P_3$ is represented in elbow portion 21 of secondary lumen LAc. It will then be understood that sections 203 and 204 of secondary lumen LAc form channels conveying the volume of fluid F2 in opposite directions. The section of main lumen LP is noted 213 in the FIG. 2.

According to one embodiment, main lumen LP can include a partial stopper positioned on a distal portion of cannula 1 enabling compensation to be made for the absence of secondary lumen LAc upstream, in order to maintain a given speed of fluid at the output of cannula 1. According to another embodiment, main lumen LP does not include a partial stopper, and the slowed injection speed relative to the flow speed of the fluid in main lumen LP in the presence of secondary lumen LAc is dimensioned in this manner.

Distance d2 in FIG. 2 represents the distance between the aperture of secondary lumen LAc and the distal end of main lumen LP. The distal portion in which there is no longer a secondary lumen is of length d2 minus the length of the elbow which can, depending on the embodiments of the cannula of the invention, vary depending on the model of the cannula of the invention. The model of the cannula can in particular vary depending on the planned procedure.

Outlet aperture 20' can advantageously be positioned, depending on cannula models 1, at different distances from end 10' of main lumen LP. Depending on the patients' builds, the choice of artery to puncture and the position of the puncture site on the said artery of cannula 1, an appropriate cannula is chosen using the following criteria:

- the diameter of distal end 10' of main lumen LP;
- predefined distance d2 between distal aperture 20' of secondary lumen LAc and distal end 10' of main lumen LP.

According to another embodiment, the length of secondary lumen LAc is much shorter than the length of main lumen LP, and is equal to a fraction of 5% to 50% of its length. According to another example embodiment, the secondary lumen can be a single elbow 21 of several centimetres, or several millimetres, upstream, diverting a fraction F2 of the liquid flowing in main lumen LP and several centimetres, or several millimetres, on return to portion 22 to guide flow F2 of diverted liquid towards aperture 20'. According to one embodiment, distal aperture 20' of secondary lumen LAc and end 10' of main lumen LP are spaced out with a distance of less than 10 cm, or less than 5 cm.

According to one embodiment, the length of the return of elbow arm 22 inside main lumen LP can be understood to be between several millimetres and several centimetres. According to one embodiment, the length of the return of elbow arm 22 is between 1 cm and 5 cm. In particular this length enables turbulence to be reduced, and to cause a laminar liquid to emerge at output 20'.

According to one embodiment, secondary lumen LAc includes an inlet 26 which is bevelled at its proximal end 20, which enables:

- the flow of liquid entering the section of secondary lumen LA to be made laminar, and/or;
- the perturbations of the flow to be reduced, or alternatively, and/or;
- the rate of flow of the reperfusion flow of the member to be stabilised and/or,
- haemolysis to be limited.

According to one embodiment, secondary lumen LAc includes a section which forms a circle or an ellipse.

According to a variant embodiment, an outer portion 25 of secondary lumen LAc is positioned outside main lumen LP. FIG. 6 represents this embodiment in which outer portion 25 includes an inlet 20 made on the lateral surface of main lumen LP and an outlet 27 made downstream from inlet 20 on the lateral surface of main lumen LP. According to this embodiment, secondary lumen LAc includes an inner portion 29 made inside main lumen LP. The embodiment of inner portion 29 is similar to the various embodiments described above in light of FIG. 2 and of FIGS. 4A to 4D. Inlet 28, also called a junction, of secondary lumen LAc which is out-of-line upstream from cannula 1 due to the presence of outer portion 25 of secondary lumen LAc, has a difference relative to the embodiment of FIG. 2.

According to one embodiment, outer portion 25 of secondary lumen LAc is fitted with a valve 24 enabling draining operations to be accomplished.

In FIG. 7 the various operating modes of such a valve are represented

According to a first operating mode, a first anterograde draining operation, noted PA, can be accomplished when flow F2 flows in the direction indicated in FIG. 5, flowing from upstream to downstream of the cannula and when valve 24 is open. According to a second operating mode, a second retrograde drain, noted PR, can be accomplished when flow F2 flows in the reverse direction to the direction indicated in FIG. 5, flowing from downstream to upstream of the cannula, when valve 24 is open. This drain operation can occur when a backflow blood flow is generated when introducing the cannula into a vessel.

According to a third operating mode, flow F2 of secondary lumen LAc is conveyed to outlet 20' when valve 24 is closed. Flow F2 runs over outer portion 25 and is reintroduced inside main lumen LP after junction 27 which enables secondary lumen LAc to be extended within main lumen LP. In this embodiment, upstream portion EXT of cannula 1 will remain outside the patient's body. In operation, portion SC of cannula 1 is subcutaneous, and portion ART corresponds to the portion introduced into a vessel such as, for example, an artery.

One advantage of this embodiment is that it is possible to benefit from a drain function enabling the satisfactory intra-arterial position of output aperture 20' to be checked, whilst having a dual-lumen cannula which avoids the need to install a reperfusion cannula. In this embodiment the cannula has two portions, one of which includes a secondary lumen LAc external to main lumen LP, to accomplish, if applicable, drainage operations, and another portion in which secondary lumen LAc is inside the main lumen to avoid a reperfusion. The embodiment of FIG. 6 has, according to one implementation, the same characteristics as the embodiment of FIG. 2, including in particular: an elbow termination, bevelled inlets and outlets, and possibly a comparable manufacturing method.

According to one embodiment, inlet 28 is extended upstream by a portion of secondary lumen LAc inside the main lumen, to take a volume of blood more easily. As an example, the inlet of secondary lumen LAc can have the same interface as that of FIG. 3 inside main lumen LP before forming an elbow towards inlet 28 of FIG. 6.

Cross-section $P_1$ represents the two sections 211, 201 firstly of the main lumen LP and secondly of secondary lumen LAc. The two portions are separated due to the fact that the cross-section is made where secondary lumen LAc forms a portion 25 external to main lumen LP.

Cross-section $P_2$ represents a cross-section identical to that of FIG. 2 since secondary lumen LAc is in this portion internal to the main lumen Cross-section $P_3$ represents a cross-section identical to that of FIG. 2 since secondary lumen LAc is in this portion inside the volume of the main lumen LP and forms an elbow similar to that of FIG. 2.

FIG. 5 represents another view of an embodiment of cannula 1 of the invention in which elbow portion 21 has been enlarged. It will be understood that volume F2 of fluid emerges in a lateral outlet 20' of main lumen LP. The direction of fluid F2 at outlet 20' of secondary lumen LAc is therefore modified with regard to the direction of the same fluid F2 upstream from the elbow. The diversion of flow F2 due to the angle formed by elbow 21 is guided towards an outgoing flow rate 2 at the outlet of secondary lumen LAc in an anterograde direction. In addition, FIG. 5 represents wall 50 of artery 5. This representation enables it to be understood that once injected, fluid F2 is directed under the effect of its kinetics into artery 5 in the direction opposite the injection of fluid F3 at the distal end of main lumen LP. The fluid is rejected at a certain speed of secondary cannula LAc and is guided:

- firstly, by the outer surface of cannula 1 and;
- secondly, by inner wall 50 of artery 5.

According to one embodiment, the material used to manufacture the lumens of injection cannula 1 of the invention is heat-sensitive semi-rigid PVC. According to one embodiment, the portion of the cannula intended to be inserted in the tissues and then in a vessel of the patient is armoured in order to prevent untimely kinkings and clampings.

One advantage of cannula 1 of the invention is that a single cannula is obtained combining the function of anterograde arterial reperfusion of the limb with the positioning of a retrograde arterial injection cannula. Systematic reperfusion significantly reduces the complications of peripheral ECMO-VA.

In addition, cannula 1 of the invention means that a single procedure combining retrograde arterial injection in the aorta and anterograde reperfusion in the limb can be established. This procedure means precious time-saving in terms of surgical, anaesthetic and resuscitation time. This single procedure enables a single arterial puncture to be made in order to accomplish the retrograde arterial injection into the aorta, and the anterograde reperfusion in the limb. The reduction of the number of punctures enables the risks of distal arterial emboli, arterial dissection, arterial thrombosis and haematoma to be reduced in the puncture site.

According to one invention of a cannula, the cannula is identical to one of the embodiments of the previous cannula, except that it is possible that the distal end may not correspond to the aperture of the main lumen LP, but includes at least outer portion 25 of secondary lumen LAc positioned outside main lumen LP. For example, the distal end of the secondary lumen can be a portion which moves between an inner position within main lumen LP for the installation of the cannula in the artery, and an outer position outside the main lumen when the latter is operating.

For example, when withdrawing an introducer, the secondary lumen changes from the inner position to the outer position.

Naturally, this cannula can have a drain valve as described for the figure

In this cannula or the cannula including the distal end of the secondary lumen corresponding to the lateral aperture of the wall of the main lumen, outer portion 25 of secondary lumen LAc positioned outside main lumen LP includes at least a portion allowing the light to pass inside the outer portion.

Thus, when the cannula is put in position the user can see whether the distal end of the secondary lumen is in the artery, due to the fact that the blood is rising up in this lumen, and is therefore passing in the outer portion which is letting the light pass. This outer portion is in fact intended to be an extracorporeal portion of the cannula.

Indeed, even if the main lumen is transparent or translucent, it can be difficult to see whether blood flows in the portion of secondary lumen located in the main lumen, and even more difficult to assess visually whether the flow rate is correct, or whether there is a fluid flow problem.

This portion can be transparent or translucent. The advantage of it being translucent is that the operator is able to determine visually the flow rate of the fluid traversing this secondary lumen.

According to an invention of a cannula, the cannula is identical to one of the embodiments of the previous cannulas, except that it can have or not have: an outer portion 25 or/and a distal end corresponding with the aperture of main lumen LP, and in that it also has an anti-backflow valve between the distal end of the main lumen and the proximal end of the secondary lumen.

This can reduce or stop blood coming out of the proximal end of the main lumen when installing the cannula.

The anti-backflow valve is not represented in the figures.

The anti-backflow valve can have an aperture or a slit enabling an introducer to be inserted into it.

The anti-backflow valve can have an aperture or a slit enabling an introducer to be inserted into it. The introducer therefore traverses the anti-backflow valve. The anti-backflow valve also includes a membrane with the opening or the slit positioned such that the walls of the membrane close the opening or the slit when the fluid pushes the membrane to the proximal end of the main light.

The membrane is positioned to allow the fluid to flow in the direction from the proximal end of the main lumen to the distal end of the main lumen.

The invention also concerns a cannula-introducer assembly including one of the three cannulas described above, and an introducer having a portion traversing the main lumen.

The invention claimed is:

1. A cannula for circulation of a fluid in an artery, comprising:
    a main lumen, conveying a volume of fluid to a first distal end;
    a secondary lumen, containing at least one inner portion positioned inside the main lumen, and partly extending parallel to the latter over a portion of the length of the main lumen, where the secondary lumen includes:
        a proximal end located downstream from a proximal end of the main lumen, so as to divert a fraction of an incoming flow rate of the fluid in the main lumen;
        an elbow portion modifying the direction of flow of the flow rate of fluid diverted by the secondary lumen relative to a direction of flow of the fluid emerging from the first end;
        a second distal end upstream from the first distal end of the main lumen, flowing out through a lateral aperture of the cannula, so as to direct the diverted fraction of the liquid in the modified flow direction, where the second distal end corresponds to the lateral aperture.

2. The cannula according to claim 1, wherein the elbow portion guides the flow diverted by the secondary lumen in a direction roughly opposite the flow flowing to the end of the main lumen.

3. The cannula according to claim 1, wherein the secondary lumen is formed of a single inner portion.

4. The cannula according to claim 1, wherein secondary lumen also includes a portion external to the main lumen positioned upstream from the inner portion, wherein the outer portion has a drain valve and is intended to be an extracorporeal portion.

5. The cannula according to claim 4, wherein the outer portion of the secondary lumen includes a first junction positioned in contact with the lateral surface of the main lumen and a second junction positioned in contact with the lateral surface of the main lumen so as to convey a fraction of the liquid externally to the main lumen between the two junctions.

6. The cannula according to claim 1, wherein the main lumen has a diameter of 5 to 7 mm, and the secondary lumen has a diameter of 0.9 to 2 mm.

7. The cannula according to claim 1, wherein the secondary lumen has a circular or elliptical section.

8. The cannula according to claim 1, wherein the proximal and/or distal end of the secondary lumen is bevelled, such that the section of the proximal and/or distal aperture of the secondary lumen is contained in a plane which is not orthogonal to the axis of one of the two lumens.

9. The cannula according to claim 1, wherein the secondary lumen has a longitudinal portion attached along a portion of the inner surface of the main lumen.

10. System for injection of a fluid into an artery, comprising:
- a cannula according to claim 1,
- a pump positioned to pump a predetermined flow rate of fluid from a sampling cannula, cooperating with an inlet of the pump via an interface tube;
- an oxygenator positioned to introduce a proportion of oxygen in a fluid, where an inlet of the oxygenator co-operates with an outlet of the pump via a second interface tube;
- a heat exchanger positioned to inject a fluid at a fixed temperature in the cannula through a third interface tube, wherein the exchanger takes the fluid from the oxygenator through a third tube.

11. The system according to claim 10, wherein at least one tube is covered with a layer of heparin.

12. The system according to claim 10, wherein the pump is positioned and configured to establish a flow rate of drawn blood.

\* \* \* \* \*